United States Patent [19]

Wolkonsky

[11] Patent Number: 4,493,427

[45] Date of Patent: Jan. 15, 1985

[54] FLASK FOR STERILE LIQUIDS

[75] Inventor: Alexander Wolkonsky, Fribourg, Switzerland

[73] Assignee: Stericric SA, Switzerland

[21] Appl. No.: 502,124

[22] Filed: Jun. 8, 1983

[30] Foreign Application Priority Data

Jun. 10, 1982 [CH] Switzerland ............... 3603/82

[51] Int. Cl.³ .................................. B65D 41/34
[52] U.S. Cl. ........................ 215/230; 215/252; 215/258; 215/31; 215/100.5; 222/571
[58] Field of Search .............. 215/230, 252, 258; 222/571; D9/349, 352, 355

[56] References Cited

U.S. PATENT DOCUMENTS

| D. 253,453 | 11/1979 | Kretz | D9/355 |
|---|---|---|---|
| D. 272,721 | 2/1984 | Grey | D9/349 |
| 2,788,161 | 4/1957 | Kemper | 222/571 |
| 2,829,807 | 4/1958 | Kirschenbaum . | |
| 2,854,163 | 9/1958 | Barnby | 222/571 X |
| 3,325,034 | 6/1967 | Squire | 222/571 |
| 3,788,510 | 1/1974 | Collins . | |
| 3,888,373 | 6/1975 | Gach et al. . | |
| 4,077,536 | 3/1978 | Brandtberg . | |
| 4,147,268 | 4/1979 | Patel et al. . | |
| 4,157,144 | 6/1979 | Weiler et al. . | |
| 4,190,169 | 2/1980 | Pehr . | |
| 4,197,960 | 4/1980 | Walter . | |
| 4,217,989 | 8/1980 | George . | |
| 4,394,923 | 7/1983 | Sugiyama | 215/354 |
| 4,436,212 | 3/1984 | Llera | 215/252 |

FOREIGN PATENT DOCUMENTS

| 2213772 | 9/1973 | Fed. Rep. of Germany . |
|---|---|---|
| 2190687 | 2/1974 | France . |
| 2290364 | 6/1976 | France . |
| 2339541 | 8/1977 | France . |
| 1316162 | 5/1973 | United Kingdom . |
| 1507540 | 4/1978 | United Kingdom . |
| 2040893 | 9/1980 | United Kingdom . |
| 1579337 | 11/1980 | United Kingdom . |
| 1592689 | 7/1981 | United Kingdom . |
| 2022063 | 9/1982 | United Kingdom . |

Primary Examiner—Donald F. Norton
Attorney, Agent, or Firm—Bacon & Thomas

[57] ABSTRACT

A flask for sterile liquids capable of supporting a terminal sterilization of pharmaceutical quality. The flask has a tamper-proof closure comprising a cap screwed on its neck and a locking ring formed in two parts axially superposed and joined by a breakable zone. One of the parts is axially carried away by the cap during opening of the flask and the other part is held axially by a shoulder formed on the neck. The cap encloses a seal made of elastomeric material inserted between its bottom and the edge of the neck, this seal being axially solid with the cap and comprising a skirt applying itself against the inner surface of the neck in a bacteriologically sealproof manner along a height sufficient to ensure a bacteriological closure seal until the locking ring is broken.

9 Claims, 8 Drawing Figures

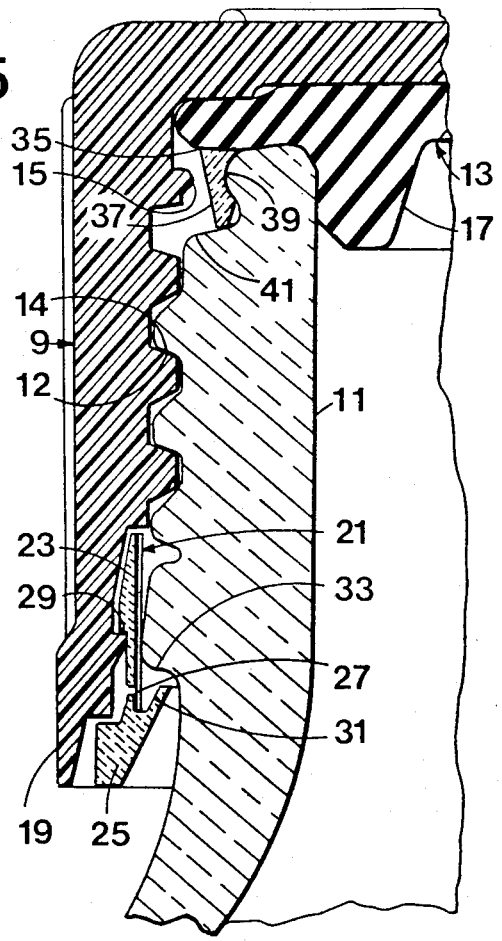
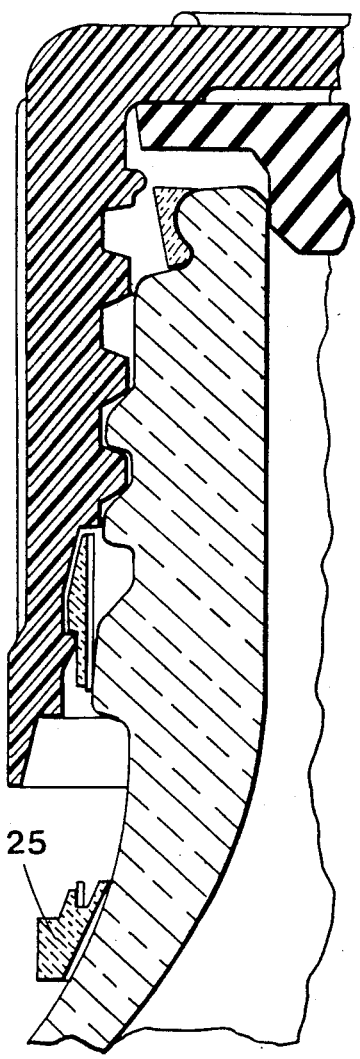
FIG.5
FIG.6

FLASK FOR STERILE LIQUIDS

The present invention relates to a flask for liquids capable of supporting a terminal sterilization of pharmaceutical quality. By "terminal sterilization of pharmaceutical quality" is to be understood a sterilization of an already filled and closed flask at a temperature of at least 120° C.

The flask according to the invention is provided with a tamper-proof closure comprising a cap, screwed on the neck of the flask, and a locking ring formed in two parts axially superposed and joined by a breakable zone, one of the parts being axially carried away by the cap during opening of the flask while the other part is held axially by a shoulder formed on the neck.

Such closure devices have already been disclosed, namely in France Pat. Nos. 2,290,364 and 2,339,541, as well as in U.S. Pat. No. 4,157,144. In the latter Patent, however, the parts of the locking ring are radially juxtaposed and concentric.

Due to unavoidable manufacturing tolerances, breaking of the locking ring takes place only after unscrewing of the cap has started. A cap thus partially unscrewed no longer ensures bacteriological sealing of the flask and there exists a possibility of contamination of the contents by external germs, this without the user being conscious of it since the locking ring is still intact. This deficiency may have serious consequences, namely in the case of liquids, such as a physiological saline solution, used in a surgical operating room.

The present invention avoids this inconveniences by the use of a seal made of elastomeric material inserted between the bottom of the cap and the edge of the flask, this seal being axially solid with the cap and comprising a skirt applying itself against the inner surface of the neck in a bacteriologically seal proof manner along a height sufficient to insure a bacteriological closure seal until the locking ring is broken.

A description of two preferred embodiments of the the invention now follows having reference to the appended drawings wherein.

Figure 1:
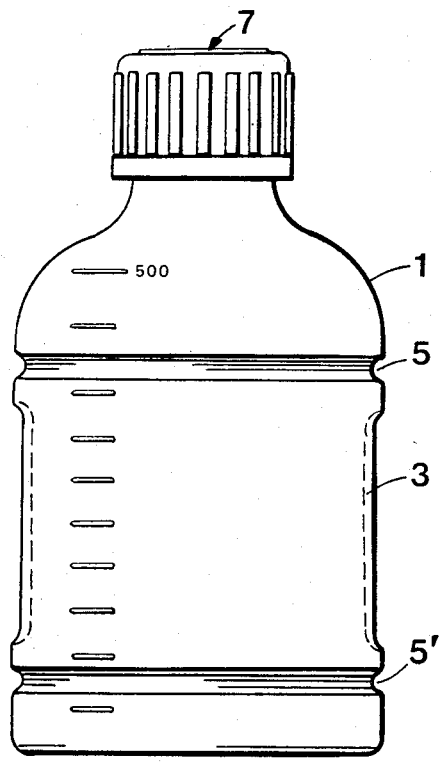
FIG. 1 is an elevation view of a flask according to a first embodiment, of which the body is made of plastic material, with a locking ring for the closure device still intact.
Figure 4:
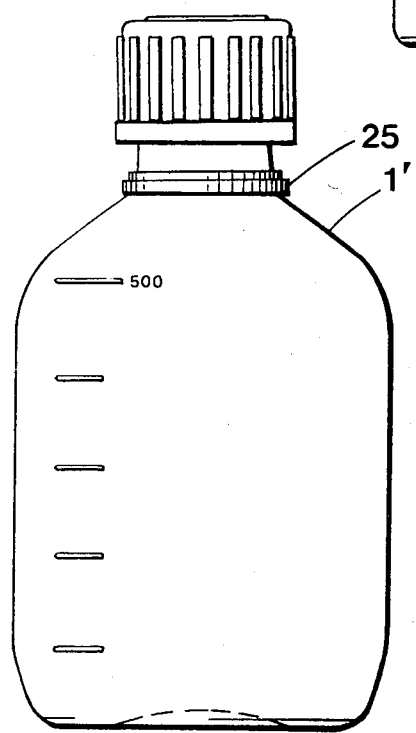
Figure 2:
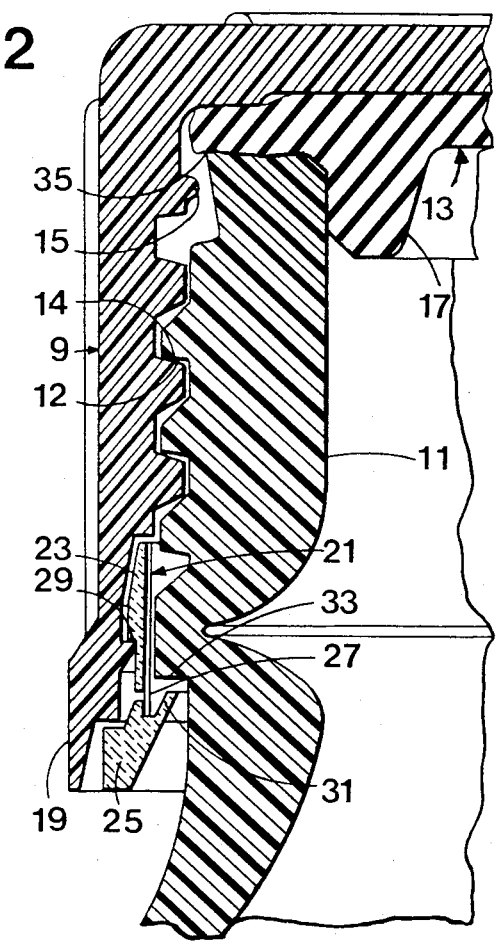
FIGS. 2 and 3 are partial axial cross-sectional views of the neck and of the closure device for the same flask, illustrated respectively before and after a first opening of the flask.
Figure 3:
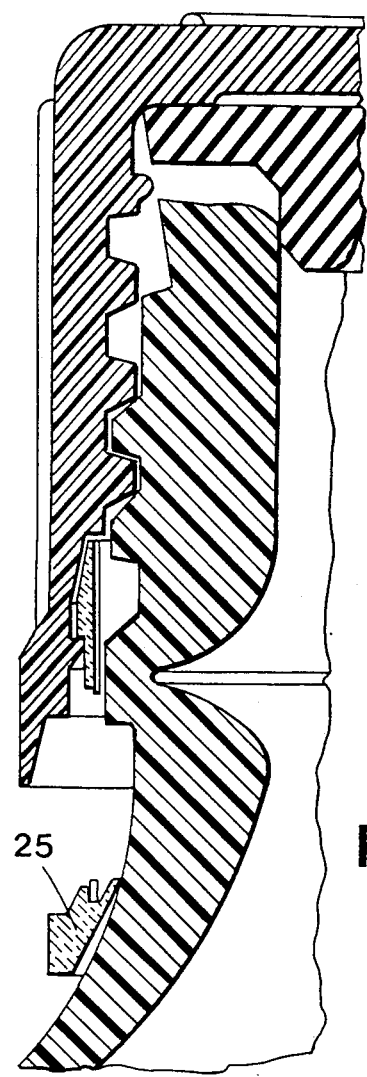
Figure 7:
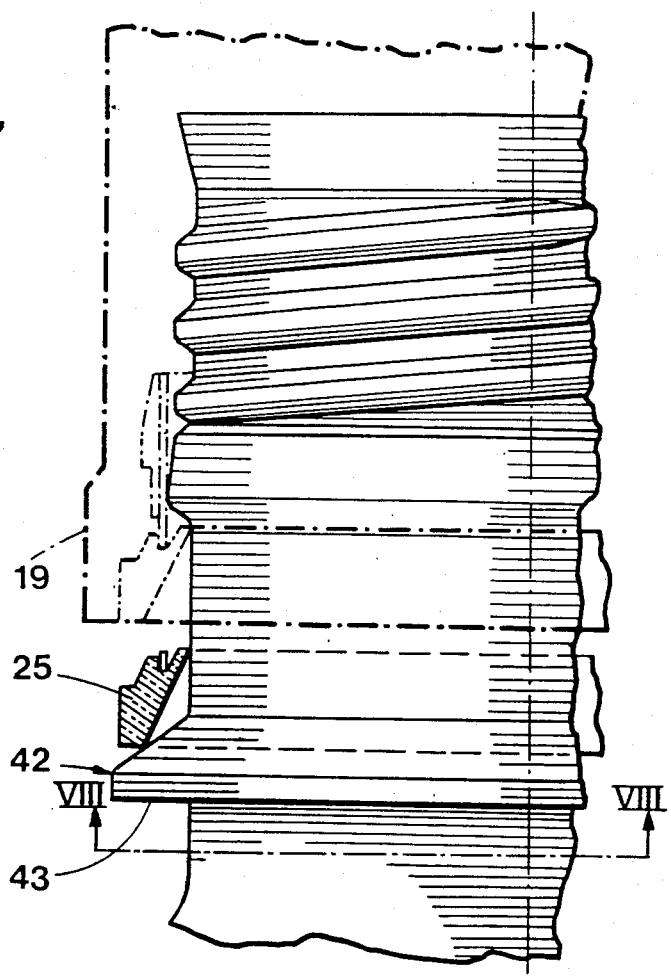

FIG. 4 is an elevation view of the flask according to a second embodiment, of which the body is made of glass, illustrated after breaking of the locking ring, FIGS. 5 and 6 are partial cross-sectional views of this second embodiment flask, similar to FIGS. 2 and 3, FIG. 7 is a fragmentary elevation view, partially in axial cross-section of a variant of the flask illustrated in FIGS. 1 to 3, and FIG. 8 is a view taken in a plane along line VIII—VIII of FIG. 7.

In FIGS. 1 to 3, the body 1 of the flask is made by blow-moulding of a water repellent hydrophobic plastic material, for example a polyolefine such as polyethylene, polypropylene or an ethylene-propylene copolymer, capable of resisting a standard pharmaceutical sterilizing operation at 120° C. The body 1 has lateral flats 3 for easy handling and two circular grooves 5 and 5' to allow for longitudinal expansion of the flask when subjected to inner pressure developing during sterilization.

The closure device 7 comprises a cap screwable on the neck 11. This cap 9 is made in molded rigid plastic material such as high density polyethylene, polypropylene, preferably loaded with talc or another mineral load. This cap has a thickness sufficient to resist the sterilization temperature and the inner pressure without unduly deforming. Furthermore, the threads are assymmetrical trapezoidal threads, of which the top face with respect to the cap, and the lower face with respect to the neck, are near to the horizontal when the flask stands upright, this being provided in order to restrict the radial force component tending to expand the cap when a high pressure prevails in the flasks. This constructional feature is especially useful in the case of a glass flask, which is described hereinafter, and which is exposed to greater inner pressures.

A seal 13 made of elastomeric material is applied on the inner face of the bottom of the cap, where it is normally retained by suction. The seal 13 is likewise axially held by a circular bulge 15. Thus, during unscrewing of the cap 9, the seal 13 rises with the cap and remains solid with it after the flask is opened.

The elastomer of the seal 13 is selected so that it withstands sterilization of the flask without important deformation, so that its elasticity does not vary practically during the stocking period and so that it does not alter the composition of the liquid which is contained in the flask and particularly so that it does not salt out too many particles or particles of too large a size.

The seal 13 comprises an annular skirt 17 which provides a bacteriologically proof joint with the inner surface of the neck 11 during unscrewing of the cap, this until the time where peripheral edge of the skirt 17 extends beyond the inner edge of the neck. The length requirements of the skirt 17 are specified hereinafter. The peripheral edge of the skirt and the inner edge of the neck are chamfered in order to facilitate fast screwing of the cap.

The cap 9 also extends into a skirt 19 in which is lodged a breakable locking ring 21. The latter is formed of two superposed parts 23 and 25, interconnected by breakable bridges 27. During unscrewing of the cap, the upper part 23 is retained in the cap by engagement with an inner shoulder 29 of the skirt 19, whereas the lower part 25 is provided with an annular inner tongue 31 which comes to butt against the lower flat face 33 of a shoulder of the neck, thereby causing simultaneous breaking of all the bridges 27 and dropping of the lower part 25 of the ring 21 on the top of the body of the flask. When the flask is closed, and the breaking ring 21 is still intact, it is completely hidden from view by the skirt 19 of the cap. When the flask is opened for the first time, the locking ring 21 breaks and its lower part 25 becomes definitely visible, as shown in FIG. 3, even after the flask is closed again, because it remains caught between the neck and the body of the flask. While the material of which the breaking bridges 27 are made must be rigid and relatively brittle, that of the parts 23 and 25 of the ring 21 must be sufficiently elastic to allow insertion of the part 23 within the skirt 19 and allow for sliding of the tongue 31 along the neck when the flask is closed for the first time. This material may be high density polyethylene, polypropylene or any other flexible plastic material able to withstand the sterilization temperature. Furthermore, the material of at least part 25 of the ring is coloured, for instance in red or in black or in any other colour that contrasts with that of the flask in order that it be clearly visible even in poor lighting conditions.

To ensure that the part 25 of the ring 21 drop under any circumstances, a sufficient radial space is provided on either side of the said part 25, due to the inner taper of the ring 19 and due to a narrowing of the neck 11 of the flask beneath the soulder 33.

As long as the locking ring 21 is still intact, it is important that a first unscrewing of the cap does not affect the bacteriological seal of the closure in any position of the flask. For this purpose, the length of the skirt 17 of the seal 13 is selected as a function of the axial clearances, prescribed by manufacturing tolerances, between on the one hand, the part 23 of the ring 21 and the inner shoulder 29 of the skirt 19 and between, on the other hand, the tongue 31 and the shoulder 33 of the neck 11, considering also the extensibility of the breakable bridges 27. The length of the skirt 17 is thus selected to provide a sufficient contact surface between it and the inner surface of the neck 11 up to and beyond the moment the ring 21 breaks, as illustrated in FIG. 3.

To avoid, once a portion of the contents of the flask has been poured and the flask is uprighted again, that drops drip along the outer surface of the neck, which could contaminate a subsequent liquid pouring, the outer edge of the neck is formed with a drop-breaking ridge 35. Viewed in axial cross-section, this ridge forms an acute angle which is defined by one side slightly inwardly inclined with respect to the vertical and a second side which is slightly inclined with respect to the horizontal, preferably by an angle of 7.5°. With such a shape and in cooperation with the water-repellent or hydrophobic nature of the plastic material of the flask, the ridge 35 counters any dripping of the liquid outside the neck. Its slope causes return in the flask of any liquid remaining on the edge of the neck.

The flask illustrated in FIGS. 4 to 6 distinguishes essentially from that of FIGS. 1 to 3 by the fact that its body 1' is made of glass of pharmaceutical quality, neutral in surface. From FIG. 4, it is seen that the lower part 25 of the broken locking ring 21 clearly stands against the flask 1'. Since glass does not have the water repellent property required for producing a dropbreaker 35, the latter is achieved by means of an added ring 37 made of a hydrophobic plastic material similar to that of which the body of the flask of FIGS. 1 to 3 is made. The ring 37 is driven into a cavity of the outer edge of the skirt, or is held by a circular bulge 39 of the skirt which engages into a circular recess of the ring 37. In closure position, the ring 37 is axially clamped between the seal 13 and a shoulder 41 of the skirt, so much so that it improves sealing.

The other parts of the flask are similar to corresponding parts of the flask of FIGS. 1 to 3 and are therefore indicated by the same reference numerals. The absence is noted however of extention grooves 5 and 5' which are of no use in the case of a glass flask. Although the manufacture by molding does not make it possible to obtain neck threads having angles as sharp as those obtainable with organic plastic material, it is seen to it that the lower face of the threads of the neck be as horizontal as possible.

Figure 8:
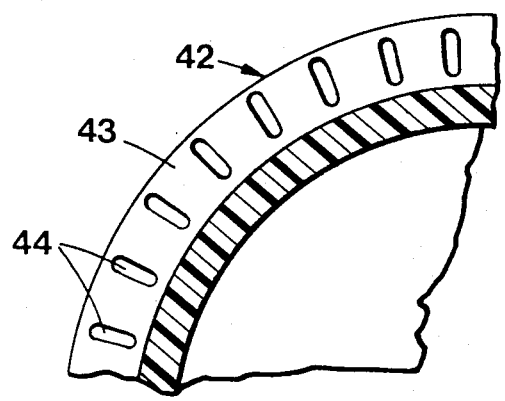

The flask shown in FIGS. 7 and 8 is similar to that described with reference to FIGS. 2 and 3 and like it, its body is made by the blow-moulding of a semi-rigid hydrophobic plastic material. Filling of the flask and screwing of its cap in an automatic machine apply to the neck of the flask an important axial force and an important rotation torque capable of causing deformation of the body which could be detrimental to proper filling and closing of the flask. In order to avoid such a deformation, there is provided a collar 42 molded simultaneously with the body of the flask and having a lower flat face 43 which, when the flask is being closed, axially bears on on an abutment member of the machine (not shown). Besides, the face 43 of the collar 42 is provided with a circular row of radial cavities 44 which come in gripping engagement with a corresponding circular set of teeth on the abutment member of the machine, in order that the rotation torque applied on the neck of the flask applies only to the abutment member of the machine and is not transmitted to the body of the flask.

It is obvious that the cavities 44 could be replaced by a set of teeth coming into engagement with cavities made on the abutment member of the machine, or could be replaced by equivalent means, such as castle-nuts, peripheral radial teeth, etc.

It will be noted that a sufficient distance has been kept between the collar 42 and the lower edge of the skirt 19 of the cap, when the latter is fully screwed, so that, after breaking of the locking ring, the lower part 25 of the latter, although it be stopped in its fall by the collar 42, be entirely visible and, due to its contrasting colour, easily distinguishes itself from the cap and the neck of the flask.

The advantages derived from a flask made according to the present invention are resumed as follows:

the flask may indifferentially be made out of glass or plastic that can resist steam sterilization.

with respect to the glass flask version and without having for that reason to place the flask under vacuum, the sterilization cycle used may be a standard cycle carried out in a conventional steam autoclave without requiring a particularly well adjusted air overpressure or without any overpressure at all, for standard temperatures and durations used in the sterilization of pharmaceutically medicated solutions in a glass flask. It is thus possible to use an already existing standard equipment and which then represents an investment saving for the manufacturer who already has such equipment at his disposition (generally of large size), or else the manufacturer may buy such an equipment at reasonable prices and rapidly start up production. He may, on the other hand, use his equipment made up of large volume injectable glass flasks without having to invest in a series of plastic flasks.

The opening/closing system of the flask according to the invention has the following features:

1. It does not have any metal parts and other tamperproof aluminum overcapsules which, upon opening of the flask, cut the thin surgery gloves and thus cause aseptic failure in the operation room.

2. It can easily and rapidly be opened by employees of tests laboratories and by the surgical dressers of an operating room who, additionally, wear wet slipping surgery gloves.

3. The open flask immediately distinguishes itself from an intact flask by the fall on the neck of the flask of the coloured lower part of the tamper-proof locking ring which is hidden from view beneath the cap screwed on a flask that has not yet been opened. This is particularly useful for users in an operating room or outside the space immediately beneath the lighting fixture where surgeons operate, the rest of the room often being dimly lighted, including the dresser's table over which are placed the surgical instruments, the cupula and the flask containing the pourable pharmaceutical medicated solutions. The users in an operating room must also very often act quickly.

4. The opening/closing system of the flask according to the invention is particularly safe as it offers a double bacteriological barrier:

screwing of the cap (1) heavily presses on the seal (2) thus on the top of the neck of the flask.

the small skirt provides another bacteriological barrier by pressing on the inside of the neck and conforming to its shape along is full height, the flask being closed.

This provides a double safety in respect to preserving sterility inside the flask, the closure device being usually the weakest point.

5. The complete closure/opening system may be assembled automatically and neatly by means of a high speed machine and under economic conditions.

6. The same assembly may be screwed by a standard screwing machine in a clean room after filling. For the glass flask version, the drop-breaking ring (6) may be set into position by a setting machine before the screwing machine, this makes it thus possible to obtain a product of very practical and safety use capable of being mass-produced at an interesting price.

As clearly shown in FIG. 4, the length of the neck is sufficient so that a segment of the latter be visible between the part 25 of the ring which rests on the body of the flask and the lower edge of the cap. Thus, the material of which the flask is made (for instance glass or polyethylene) is visible on either side of the part 25, so much so that the latter, due to its contrasting colour, clearly strikes out in poor lighting conditions.

In a not-shown variant of the flask of FIGS. 1 to 3 made of plastic material, the lateral wall of the body 1 comprises a short frustoconical lower part merging with the bottom of the flask as is the case for the body 1' of the glass flask of FIGS. 4 to 6. This frustoconical part is intended to be clamped in a corresponding female frustoconical part of a closing machine in order that the flask be solidly retained angularly as well as axially during closure thereof.

The embodiments of the invention in which an exclusive property or privilege is claimed are defined as follows:

1. A flask for sterile liquids capable of supporting a terminal sterilization of pharmaceutical quality, comprising a body provided with a neck, a tamper-proof closure comprising a cap screwed on the neck of the flask, and a locking ring formed in two parts axially superposed and joined by a breakable zone, one of the parts being axially carried away by the cap during opening of the flask and the other part being held axially by a shoulder formed on the neck, characterized in that the cap encloses a seal made of elastomeric material capable of withstanding sterilization of the flask without important deformation, said seal being inserted between the bottom of the cap and the edge of the neck; the seal is axially held by the cap and comprises a skirt applying itself against the inner surface of the neck in a bacteriologically sealproof manner along a height sufficient to ensure a bacteriological closure seal until the locking ring is broken; the locking ring in unbroken condition is completely concealed by the cap; a radial clearance is provided on either side of the locking ring, which is sufficient so that, after breaking of the locking ring, that part of the ring which is held by the neck shoulder falls and rests on a shoulder of the flask when the flask stands upright, and the said falling part is of a colour contrasting with that of the flask, and the length of the neck being sufficient for a segment of the neck to be visible between that part of the ring resting on the shoulder of the neck and the lower edge of the cap when the said cap is secured back on the neck.

2. A flask according to claim 1, characterized in that the body of said flask is made of glass and a drop-breaking ring made of hydrophobic material is housed within a peripheral cavity of the edge of the neck, this drop-breaking ring having a sharp peripheral edge and being axially clamped between the said seal and an annular shoulder of the neck when the flask is closed.

3. A flask according to claim 2, characterized in that said body comprises a lateral wall and an essentially flat bottom, and the lateral wall comprises a major cylindrical part and a minor frustoconical part, the said frustoconical part having a large transverse base merging with said cylindrical part and a small transverse base merging with said bottom.

4. A flask according to claim 1, characterized in that the body of said flask is made of semi-rigid hydrophobic material and the upper part of said neck is formed with a sharp dropbreaker.

5. A flask according to claim 4, characterized in that the neck is provided with a collar spaced from said shoulder, said collar being integrally molded with the body of the flask and having a lower flat face perpendicular to the axis of the flask.

6. A flask according to claim 5, characterized in that the collar is provided with gripping means capable of angularly securing said collar with an abutment member of a filling machine.

7. A flask according to claim 6, characterized in that said body comprises a lateral wall and an essentially flat bottom, and the lateral wall comprises a major cylindrical part and a minor frustoconical part, the said frustoconical part having a large transverse base merging with said cylindrical part and a small transverse base merging with said bottom.

8. A flask according to claim 5, characterized in that said body comprises a lateral wall and an essentially flat bottom, and the lateral wall comprises a major cylindrical part and a minor frustoconical part, the said frustoconical part having a large transverse base merging with said cylindrical part and a small transverse base merging with said bottom.

9. A flask according to claim 4, characterized in that said body comprises a lateral wall and an essentially flat bottom, and the lateral wall comprises a major cylindrical part and a minor frustoconical part, the said frustoconical part having a large transverse base merging with said cylindrical part and a small transverse base merging with said bottom.

* * * * *